United States Patent [19]

Khabirova

[11] Patent Number: 4,893,615
[45] Date of Patent: Jan. 16, 1990

[54] OXYGENATION AND RELAXATION CABIN

[76] Inventor: Lioutsia Khabirova, 17 allée de l'Arlequin, 92000 Nanterre, France

[21] Appl. No.: 180,983
[22] PCT Filed: Jul. 24, 1987
[86] PCT No.: PCT/FR87/00294
  § 371 Date: Mar. 23, 1988
  § 102(e) Date: Mar. 23, 1988
[87] PCT Pub. No.: WO88/00480
  PCT Pub. Date: Jan. 28, 1988

[30] Foreign Application Priority Data
  Jul. 24, 1986 [FR] France .................. 86 10765

[51] Int. Cl.⁴ .................. A61H 1/00; A61H 21/00
[52] U.S. Cl. .................. 128/24.2; 128/24.1; 128/202.12; 128/202.27
[58] Field of Search .......... 128/24.2, 24.1, 202.12, 128/202.27

[56] References Cited
U.S. PATENT DOCUMENTS

| 314,453 | 3/1885 | Ketchum | 128/202.12 |
| 365,067 | 6/1887 | Harris | 128/202.12 |
| 904,172 | 11/1908 | Batter | 128/202.12 |
| 1,827,530 | 10/1931 | Grond | 128/202.12 |
| 3,826,250 | 7/1974 | Adams | 128/24.2 |
| 3,903,869 | 9/1975 | Bancolord | 128/202.12 |
| 4,559,939 | 12/1985 | Levine et al. | 128/202.27 |
| 4,712,538 | 12/1987 | Hardie et al. | 128/24.1 |

FOREIGN PATENT DOCUMENTS

| 276202 | 7/1914 | Fed. Rep. of Germany . |
| 842528 | 6/1952 | Fed. Rep. of Germany . |
| 1161427 | 8/1958 | France . |
| 1181275 | 6/1959 | France . |

Primary Examiner—Edgar S. Burr
Assistant Examiner—Kimberly L. Asher
Attorney, Agent, or Firm—Dennison, Meserole, Pollack & Scheiner

[57] ABSTRACT

Oxygenation and relaxation cabin intended to be used in urban areas or in an environment where pollution is relatively high. The cabin is constituted by a closed enclosure provided with a lockable door (20) associated with a prepayment device (16) and includes means (26, 44) for supplying pure air with an odor chosen by the customer, together with audio-visual relaxation means. The cabin in accordance with the invention is intended to be used in urban areas, in a workshop, in a factory, etc.

3 Claims, 2 Drawing Sheets

OXYGENATION AND RELAXATION CABIN

FIELD OF THE INVENTION

The invention relates to an oxygenation and relaxation cabin for use, in particular, in an urban area or in any other location where air pollution is relatively high.

PRIOR ART

In large urban agglomerations, in some workshops, and in some factories, people are subjected to permanent stress that can sometimes reach a very high level, due to air pollution, noise, crowding, etc. . . . .

There is no current means for easily escaping from these stresses, even temporarily.

SUMMARY OF THE INVENTION

The invention seeks to satisfy this want.

The invention provides an oxygenation and relaxation cabin providing a person with temporary isolation and relaxation away from atmospheric pollution, noise, crowding, etc.

To this end, the present invention provides an oxygenation and relaxation cabin for use, in particular, in an urban zone or in an environment having relatively high pollution, the cabin being characterized in that it is constituted by a closed enclosure fitted with a lockable door equipped with a payment device, and in that it contains means for supplying pure air to which a given odor selected by the customer may optionally be added, adjustable lighting means, and control circuits for these various means enabling them to operate for a predetermined period of time after payment of a corresponding sum and after parameter selection by the customer.

Cabins of this type may be installed in urban areas or in particularly tiring environments to provide, in return for moderate payment determined as a function of the duration of use, oxygenation and nervous relaxation giving rise to a sensation of comfort, rest, and well-being.

In a first embodiment of the invention, the means for supplying air comprise cylinders of compressed air connected via respective expanders and meters to a control circuit including a panel for enabling the customer to select an odor.

In a variant, these means for supplying air comprise a compressed air supply network coming from a central station for filtering, purifying, and compressing air, said network being connected to the cabin at a control circuit via an expander and a meter and optionally via a device for adding and mixing in a given odor.

The air supply means may be provided in several ways: they may terminate in one or more flexible hoses provided with face masks that may be removable and discardable after use for reasons of hygiene, or else the air supply means may be connected to air-delivering outlets or vents disposed in the immediate vicinity of the customer's face.

Advantageously, the inside of the cabin includes a selection panel placed within reach of a seat for receiving the customer, said panel serving for selecting an odor for the air, or a musical background, for adjusting the volume of the musical background, and also for adjusting the intensity of the lighting and optionally for opening a portion of the roof of the cabin and for projecting a fixed or an animated image on a screen.

Means are also provided for renewing the air in the cabin, at least in part, each time it is used.

The payment device may be of any suitable type, for example a credit card device or a coin mechanism.

BRIEF DESCRIPTION OF THE DRAWINGS

Other details, characteristics, and advantages of the invention appear more clearly on reading the following description which is made by way of example and with reference to the accompanying drawings, in which.

BEST METHOD OF PERFORMING THE INVENTION

Figure 1:
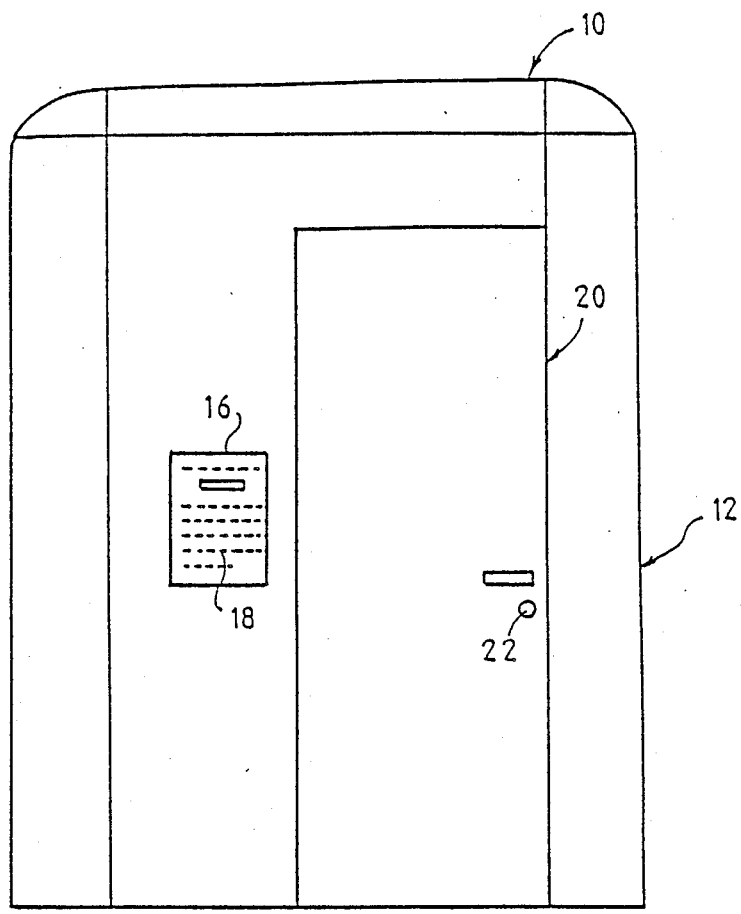
FIG. 1 is a diagrammatic front view of a cabin in accordance with the invention.
Figure 2:
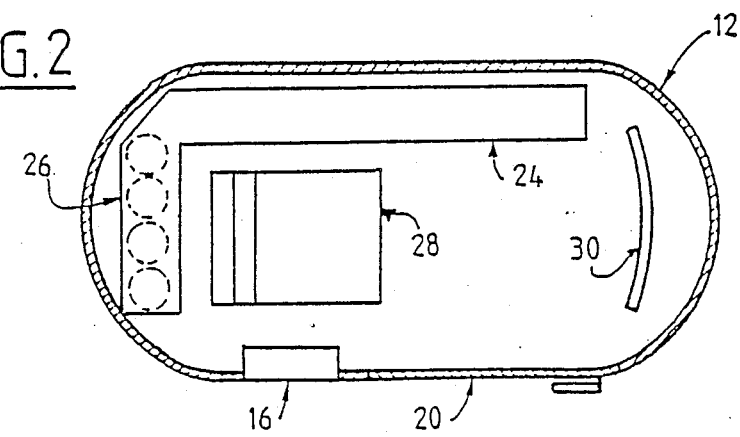
FIG. 2 is a diagrammatic plan section of the cabin.

The cabin 10 shown in the drawings is of the type intended to be used in an urban agglomeration, for example, and constitutes a closed enclosure placed on and fixed to the ground. It is of sufficient size for a person to feel at ease therein. The roof of the cabin is made of translucent or transparent materials, for example an unbreakable tinted glass, and includes opening portions, as described below. The vertical wall 12 of the cabin preferably includes heat and sound insulation, and its floor 14 is of a type that can easily be cleaned.

Cabin wall 12 has a payment device 16 on its outside face suitable for receiving a credit card or coins, for example, together with instructions 18, enabling a door 20 provided with a locking system 22 to be opened after payment of a sum which is determined as a function of the desired duration of cabin use.

When the cabin is used in a workshop or in a factory, for example, the payment device 16 may be designed to accept tokens, magnetic cards, or any other means made available to people working or spending time in the workshop or the factory.

The inside of the cabin is fitted with a panel 24 for selection and control purposes, means 26 for supplying pure air, a seat 28, and optionally a screen 30 placed facing the seat 28 together with means 32 for projecting a fixed or an animated image on the screen.

Further, lighting means and heating means for use in winter (not shown) are also provided inside the cabin. The cabin is conventionally connected to the electricity supply mains.

The selection and control panel 24 includes, for example, keys 34 for selecting a given odor or scent corresponding to the type of air that a person desires to breathe (e.g. meadow air, forest air, sea air, mountain air, etc. . . . ), keys 36 for selecting a predetermined background sound (music, a flowing river, breakers, etc. . . . ), and knobs 38 and 40 for controlling the projection of an image and for adjusting the brightness of the lighting and the sound volume.

The panel 24 may also be fitted, at the top thereof, with a strip of lights of the advertising type for displacing a message or other announcement. One or more loudspeakers 42 for providing sound output may be mounted above the panel 24 or else on either side of the seat 28.

The air supply means 26 comprise, for example, a series of cylinders of compressed air 44 each corresponding to a given odor or scent and received in a cupboard 46 placed inside the cabin and provided with respective expanders 48, meters 50, and taps 52 (e.g.

electrically controlled valves) with the opening and closing thereof being controlled from the panel 24. Each tap 52 is equipped, for example, with a flexible hose 54 having a removable face mask 56 fitted to the end thereof. Each flexible hose may be of the type suitable for being wound automatically into the cupboard 46, with means being provided for holding it in the extended position and for causing it to be wound back in after use, e.g. by pressing a key.

In this case, the panel 24 also includes a mask dispenser 58 and a drawer 60 for receiving used masks.

In a variant, the cabin may be connected to a pure compressed air network which is supplied from a central station for filtering, purifying, and compressing air. In this case, a plurality of cabins of the same type may be supplied from a common central station. Each cabin is connected to the compressed air network via an expander, a meter, and a tap of the same type as described above, and may also include means for adding or mixing in with the air supplied from the network, a given odor or scent which is preferably non-chemical.

Figure 3:
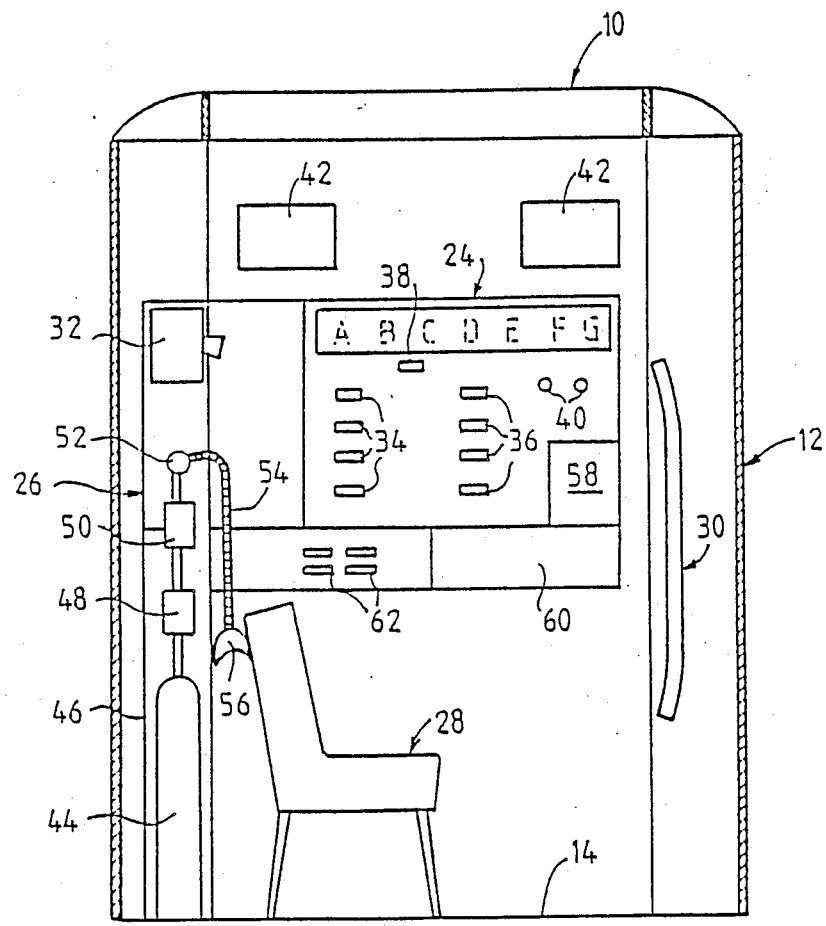
FIG. 3 is a diagrammatic vertical section of the cabin.

Air delivering openings or vents such as those referenced 62 in FIG. 3, may also be provided for people who do not like putting on a face mask for the purpose of blowing pure air at a low flow rate and speed into the cabin in the immediate vicinity of the face of a person sitting on the seat 28.

The cabin in accordance with the invention may also be fitted with automatic means for at least partially renewing the air contained in the cabin after it has been used by a person.

The cabin operates as follows:

When the cabin is unoccupied, the door 20 is locked, and the light inside the cabin may be switched off with all the other means contained therein being at rest. A person desiring to use the cabin inserts a credit card (or coins) in the payment device 16 for an amount corresponding to a determined period of cabin use. After the coins have been accepted, or after a debit has been recorded on the card holder's account and the card has been returned, the payment device 16 causes the door 20 to be unlocked and activates the selection and control panel 24. The opening and closing of the door 20 may be taken into account for indicating whether a person is legitimately inside the cabin.

The person can then use the various keys on the panel 24 to select the odor or scent of the air to be breathed, the type of background music or sound to be heard, and also the brightness of the lighting and the volume of the background music or sound. The panel is also used for controlling projection on the screen 30, for optionally partially opening the roof 10 of the cabin, etc.

When the air supply means comprise one or more flexible hoses 54 to which a mask should be fitted, the person takes a new mask from the dispenser 58, fixes it to the end of the flexible hose 54 and can then apply the mask to the face or else hold it in front of the nose and mouth.

When the air feed means do not include flexible hoses, the air is diffused automatically through the openings or vents 62 in the vicinity of the head of the person sitting in the seat 28. It is also possible to provide both of these possibilities simultaneously, together with a selection key for switching from one to the other.

The person sitting in the seat 28 may remain in the cabin for a certain length of time breathing pure air in a pleasing sound ambience and, if so desired, looking at images that may be projected on the screen 30.

The end of the paid-for stay in the cabin is indicated by the air supply being switched off together with the sound and the projection of images.

The person must then leave the cabin and allow the door to close. This opening and closing of the door 20 can be taken into account to indicate that the person has left the cabin after using it, and to cause the air in the cabin to be partially or totally renewed, e.g. by switching on a fan.

The heating means provided in the cabin may be of the electrical type, for example, and may be switched on as soon as the person desiring to use the cabin has paid.

In general, the fittings and decoration inside the cabin should be designed to give a sensation of calm and well-being. The outside shape of the cabin should be selected to meld as well as possible with its environment, whether that be an urban agglomeration or a workshop.

I claim:

1. In a controlled environment enclosure wherein an occupant may selectively control and regulate environmental conditions within the enclosure, the combination comprising a closed housing including an access door for ingress and egress to and from the interior of said housing, occupant support means within said housing, self-contained air supply means for said enclosure including means for selectively delivering said air generally into said housing or directly to a user oriented delivery mask, means for regulating and varying the quality and condition of the air supplied by said air supply means, variable lighting means within said housing controllable by the occupant, audio-visual generating means and control means therefor in said housing operable by the occupant, check controlled latching means for said access door to said housing variable to enable a user to select a predetermined occupancy period in response to payment of a corresponding sum of money, timing means interconnected between said latch and the various control devices within said housing to initiate and terminate actuation thereof in accord with the predetermined occupancy period selected and paid for by the user, and means associated with said access door and responsive to opening of said access door for actuating said air supply means at the end of each user occupancy to provide a fresh supply of air for a subsequent occupant.

2. A cabin according to claim 1, characterized in that the means for supplying air comprise cylinders (44) of compressed air connected via respective expanders (48) and meters (50) to a control circuit including a panel (24) for enabling the customer to select an odor.

3. The invention defined by claim 1 wherein the user oriented delivery masks are disposable.

* * * * *